United States Patent [19]

Mazur et al.

[11] Patent Number: 5,116,745
[45] Date of Patent: May 26, 1992

[54] PROCESS FOR PREPARING 2-ACYLGLYCERIDES OR 1,2-DIACYL DIGLYCERIDES OR 2,3-DIACYL DIGLYCERIDES

[75] Inventors: Adam W. Mazur; George D. Hiler, II; Magda El-Nokaly, all of Cincinnati, Ohio

[73] Assignee: The Procter & Gamble Company, Cincinnati, Ohio

[21] Appl. No.: 511,115

[22] Filed: Apr. 19, 1990

[51] Int. Cl.$^5$ .................... C12P 7/64; C12P 7/62; C12N 9/20
[52] U.S. Cl. ........................... 435/134; 435/198
[58] Field of Search ................ 435/134, 135, 198

[56] References Cited

U.S. PATENT DOCUMENTS 4,865,978 9/1989 Serota ..................... 435/134

FOREIGN PATENT DOCUMENTS 64855 11/1982 European Pat. Off. .
126416 11/1984 European Pat. Off. .
237092 9/1987 European Pat. Off. .
0321777 6/1989 European Pat. Off. .
0234590 11/1985 Japan .
1019042 1/1989 Japan .

OTHER PUBLICATIONS

Grant and Hackh's, *Chemical Dictionary*, Fifth Edition, p. 40, 1987.
Lazar et al., Proc-World Conference on Emerging Technologies in the Fats and Oil Industry, "Synthesis of esters by liposes", pp. 346–354, 1986.

*Primary Examiner*—David M. Naff
*Assistant Examiner*—Mike Meller
*Attorney, Agent, or Firm*—Rose Ann Dabek; Jerry J. Yetter; Richard C. Witte

[57] ABSTRACT

A process for the selective hydrolysis of triglyderides to 2-acyl glycerides is disclosed. This process uses a primary lower alkyl alcohol selected from the group consisting of methanol, the primary butanols and the primary pentanols and 2-butanol, an aqueous buffer system and a 1,3-lipase. The 2-acylmonglycerides can be used to make stereospecific 1,2-diacyl glycerides or 2,3-diacyl glycerides through esterification with acid anhydrides and 1,3-lipase catalysis. Stereospecific 1,2,3-triglycerides can be made from these materials by standard esterification reactions under conditions which control rearrangement.

14 Claims, No Drawings

PROCESS FOR PREPARING 2-ACYLGLYCERIDES OR 1,2-DIACYL DIGLYCERIDES OR 2,3-DIACYL DIGLYCERIDES

FIELD OF THE INVENTION

This invention relates to a lipase-catalyzed regio- and stereoselective preparation of triglycerides. These triglycerides are prepared by a synthetic route which involves regioselective hydrolysis of triglycerides to 2-acyl monoglycerides followed by regio- and stereoselective acylation of 2-acylglycerides to obtain specific triglyceride compounds.

BACKGROUND OF THE INVENTION

Monoglycerides are important food ingredients and surfactants. They are widely used in foods for emulsifiers and are found in salad dressings, creams, frozen desserts, shortenings and baked goods. Monoglycerides are used for forming stable emulsions of oil and water as well as for complexing with starch and proteins. In addition, monoglycerides are useful for the synthesis of di- and triglycerides which are used in foods, drugs, and other consumer products. Monoglycerides can also be used to derivatize other materials.

It has long been known that enzymic conversion of triglycerides to glycerol and fatty acids with 1,3-specific lipases, produces 2-monoglycerides as intermediates. However, only recently has this reaction been examined for practical preparation of 2-monoglycerides. In general these reactions have been carried out by transesterification or hydrolysis in mechanically formed microemulsions using enzyme catalysis. Both methods require nearly anhydrous conditions.

The stereoselective acylation of 2-monoglycerides to form regiospecific triglycerides is also important. Cocoa butter substitutes, low calorie fats and other tailored triglycerides require such a synthesis.

BACKGROUND ART

European Patent Application 126.416 (Asahi Denka Kogyo, 1984) describes a continuous transesterification of fat or oil using lipase enzymes. The lipase has 1,3-specificity and is fixed on a porous solid or Chitosan derivative as a carrier. Preferably alcohols are added during the reaction. The most preferred alcohols are aliphatic alcohols having 4–18 carbons. The preferred are butyl, hexyl, octyl and decyl alcohols. The level of alcohol is 50–90 mol% of the free fatty acid estimated to be produced. The level of water is controlled so that 1,2-diglycerides are formed. Fatty acid is then added to make triglycerides. The water activity of the reaction mixture is from 0.5 to 0.9.

U.S. 4,865,978, issued to Serota (assigned U.S. Agricultural Department, 1989) describes the hydrolysis of triglycerides to fatty acid and glycerol with lipase through the formation of a "pseudo emulsion". The oil phase is divided into emulsion size particles suspended in the aqueous phase during mixing. These particles rapidly coalesce upon termination of the mixing. The reaction is carried out at temperatures of 20° C. to 45° C.

European Patent Application 64,855, issued to Halling et al. (assigned Unilever, 1982) discloses transesterification of fats by reaction in a water-immiscible organic liquid in contact with an enzyme in a water phase (containing no more than 4% water). Glycerides are transesterified with a lipase enzyme in the presence of fat, oil or fatty acid. The lipase is immobilized on a solid.

Japanese 62,061,591 (assigned Kao, 1985) describes an interesterification reaction using an enzyme in the presence of water, dihydric or trihydric alcohol (glycol or glycerol). The enzyme used is obtained by adding a water-insoluble carrier to a lipase containing medium which is then dried.

Japanese 61,173,791 (assigned Kao, 1986) describes the method for non-specific hydrolyzing oils using lipase in which the aqueous phase contained from 10% to 40% glycerine. After hydrolysis an oily layer, an emulsion and an aqueous layer are formed. The emulsion layer is recovered and reused.

Japanese 62,278,988 (assigned Kao, 1987) discloses an enzymic or microbial reaction. Two phases are prepared, a non-aqueous solution and an aqueous solution. The reaction occurs at the interface of these two phases.

European patent application 237,092, filed by Holmberg (assigned Berol Kemi, 1987) describes a transesterification of triglycerides which is carried out in the presence of a lipase with a hydrophobic part (organic solvent) and a surface active component in water under strictly controlled conditions. Hexane is used for the hydrophobic material. Both surfactants and auxillary surfactants are used. Alcohols and glycol ethers are listed as surface active components, including butanol, pentanol and hexanol.

In general, the described processes require low water activity or other strictly controlled conditions. No practical methods were available to control the ratio of 2-acylglyceride to 1,2-diglycerides over a broad range. Although methods involving microemulsions reportedly gave good yields of 2-acyl glycerides, it was necessary to separate the monoglyceride from the surfactant. This may not be easy due to the tendency of 2-acyl glycerides to rearrange to 1-acylglycerides when heated.

Accordingly, an economical process that would produce relatively pure 2-monoglycerides in high yield is desirable. The ability to produce high yields of 2-acylglycerides with little or no 1,2-diacyl-glycerides or free glycerol is also highly desirable. It has been found that if the reaction is carried out in the presence of a lower alkyl alcohol selected from the group consisting of methanol, primary butanols and pentanols, and 2-butanol, the reaction proceeds in high yield to 2-acylglycerides. The triglyceride is suspended in a water immiscible solvent, for example, hexane, and the lipase is dissolved in an aqueous buffer. The alcohol is added to the reaction mixture. It is surprising that this reaction occurs without the presence of added emulsifiers or surfactants, and the lipase can be recovered and reused.

A clear advantage of this new process is ability to control the course of hydrolysis by influencing the form of microstructures present in the reaction mixture. The hydrolysis generates products such as diglycerides, monoglycerides and acids known to undergo spontaneous formation of association structures, aggregates, microemulsions or liquid crystals if conditions permit. In particular, the presence of an alcohol modifies these microstructures, for example, it causes transition of liquid crystals to microemulsions. These phenomena can have a profound effect on a course of the hydrolysis reaction. Thus, the control of hydrolysis can be achieved by proper selection of solvents, the alkyl alcohols described herein, without addition of emulsifiers.

It is accordingly an object of this invention to produce 2-acylmonoglycerides in yields of 80% or more.

Another aspect of this invention is the acylation of the monoglyceride in the presence of an enzyme with an acid anhydride to 1,2-diglycerides. 2-Acylglycerides can be isolated from the reaction mixture and used in the organic solvent in an acylation reaction using acid anhydrides.

Accordingly, it is the object of this invention to prepare regioselective 1,2-diglycerides or 2,3 diglycerides. These diglycerides can then be esterified to produce triglycerides through the use of a normal esterification reaction using acid chlorides or acid anhydrides. This esterification can be carried out using enzymic or chemical catalysts.

All percentages herein are by weight unless otherwise indicated.

These and other objects of this invention will become obvious from the descriptions herein.

SUMMARY OF THE INVENTION

Described herein is a process for preparing 2-monoglycerides by enzymic hydrolysis comprising the steps of:

(1) preparing an aqueous solution of a lipase enzyme having a pH of 4 to about 8;

(2) forming a mixture of a water immiscible hydrocarbon, a lower alkyl alcohol selected from the group of methanol, primary butanols, primary pentanols and 2-butanol, and a triglyceride;

(3) mixing the solutions from about 20° C. to about 50° C. for at least one hour; and (4) separating the phases and optionally recovering the 2-acylglyceride from the organic phase.

Also disclosed is a process for acylating a 2-acylglyceride by reacting an acid anhydride, immobilized lipase in a water immiscible solvent for from about 0.5 hours to about 5 hours at from about 20° C. to about 50° C. temperature to form a stereoselective 1,2-diacylglyceride or 2,3-diglyceride.

Stereospecific 1,2,3-triacyl glycerols can be prepared by reacting the 1,2-diglycerides or 2,3-diglyceride with an acid anhydride or an acid chloride under anhydrous conditions in the presence of a chemical catalyst, e.g., 4-N,N-dimethylaminopyridine or an enzymic catalyst.

DETAILED DESCRIPTION OF THE INVENTION

Triglycerides prepared according to this invention generally have the formula:

werein R stands for an alkyl saturated or unsaturated fatty acid acyl group. R, R' and R" can be equal to each other.

The alkyl fatty acids used herein preferably have from about 2 to about 24 carbon atoms. Most preferably, the fatty acid in the 2 position has from 8 to 24 carbon atoms and fatty acids in the 1 and 3 positions, i.e. R and R", have from 8 to 24 carbon atoms. The fatty acids can be either saturated or unsaturated. The unsaturated fatty acids can be mono unsaturated fatty acids or polyunsaturated fatty acids. The position occupied by R and R" are the 1 and 3 positions, the position occupied by R' is the 2 position.

A. Definitions

By "2-acylmonoglyceride" or "2-acylglyceride" is meant a glycerol molecule esterified on the second carbon atom with a medium or long chain fatty acid.

By "medium chain fatty acid," as used herein, is meant a saturated fatty acid, unsaturated fatty acid, or mixture thereof, having 6 to 10 carbon atoms.

By "medium chain fatty acid anhydride" as used herein, is meant the dehydration product of two medium chain fatty acids.

By "medium chain saturated fatty acid," as used herein, is meant $C_6$ (caproic), $C_8$ (caprylic), or $C_{10}$ (capric) saturated fatty acids, or mixtures thereof. The $C_7$ and $C_9$ saturated fatty acids are not commonly found, but they are not excluded from the possible medium chain fatty acids. The present medium chain fatty acids do not include lauric acid ($C_{12}$), sometimes referred to in the art as a medium chain fatty acid.

By "long chain fatty acid," as used herein, is meant a saturated fatty acid, unsaturated fatty acid, or mixture thereof, having 14 to 24 carbon atoms.

By "long chain saturated fatty acid," as used herein, is meant $C_{18}$ (stearic), $C_{19}$ (nonadecylic), $C_{20}$ (arachidic), $C_{21}$ (heneicosanoic), $C_{22}$ (behenic), $C_{23}$ (tricosanoic), or $C_{24}$ (lignoceric) saturated fatty acids, or mixtures thereof.

As used herein, the term "comprising" means various components or steps can be conjointly employed in the present invention. Accordingly, the term "comprising" encompasses the more restrictive terms "consisting essentially of" and "consisting of."

All percentages, ratios and proportions used herein are by weight unless otherwise specified.

HYDROLYSIS OF TRIGLYCERIDES TO 2-MONOACYLGLYCERIDES

Hydrolysis of triglycerides to 2-monoacylglyceride is carried out in a two phase mixture of hydrocarbon and the starting triglycerides in a water immiscible phase and an aqueous phase comprising the buffer and a 1,3-specific lipase. The lower alkyl alcohol partitions between the aqueous phase and the organic phase.

The presence of alcohol has two functions. It inhibits hydrolysis of 2-acylglycerides to glycerol and it drives the reaction towards 2-monoglyceride. In its absence, the process reaches early steady state characterized by high concentrations of triglycerides and diglycerides. Thus, extension of the reaction time in the absence of alcohols would not result in better yields of di- or monoglycerides but in the formation of glycerol. The higher straight chain alkyl alcohols, those having six or more carbon atoms, are less efficient or do not work. The alcohols that can be used herein are methanol, the primary butyl alcohols and the primary pentyl alcohols and 2-butanol. The preferred alcohols are 1-butanol, isobutanol and secondary butanol. The propyl alcohols do not work in this reaction nor does ethanol.

The primary butanols are 1-butanol and 2-methyl-1-propanol. The primary pentanols are 1-pentanol, 2-methyl-1-butanol, and 3-methyl-1-butanol. The only secondary alcohol that functions to produce the high yields of 2-acyl glycerides in the process of this invention is 2-butanol.

Any 1,3-specific lipase can be used for the hydrolysis. The lipases derived from the species aspergillus and rhizopus can be used. Specific lipases include aspergillus oryzae, aspergillus niger, mucor javanicus, mucor miehei, pancreatic, rhizopus delamar, rhizopus japonicus. These include MAP from Amano (Japan), lipolase and lipozyme from Novo (Netherlands). The amount of enzyme used is the amount of enzyme necessary to catalyze the reaction at a reasonable rate. Too slow a rate will cause the concentration of diglycerides to increase.

The enzyme concentration depends upon the amount of active protein in the enzyme preparation. Enzyme can be dried, immobilized on a resin or covalently bonded to or absorbed on a support, or be in solution. The concentration needed to hydrolyze the triglyceride depends upon the form, the type and the activity of the enzyme. The amount required is a catalytic amount. A catalytic amount is enough to have the enzyme produce required 2-acyl glyceride at a reasonable rate but not so much as to force the reaction to form glycerine. One skilled in the art can easily determine the catalytic amount by running a small scale reaction and looking at the final products.

The triglyceride which has the requisite alkyl fatty acid in the 2 position is dissolved in a hydrocarbon. The preferred hydrocarbons are the hexanes, petroleum ether, or isooctane. Any water immiscible hydrocarbon solvent which is essentially inert to the lipase can be used. Some solvents can denature enzymes. The solvent must dissolve the triglyceride at the temperature of the reaction. Since these triglycerides can be used in foods and pharmaceuticals, a food approved or edible hydrocarbon should be used. The hydrocarbon can be an alkane with from 5 to 10 carbons, an aromatic hydrocarbon such as benzene, toluene or xylene or halogenated hydrocarbons such as chloroform, methylene chloride or carbon tetrachloride. The preferred hydrocarbon solvents are hexane, pentane, petroleum ether and isooctane.

From about 3% to about 60% triglyceride is used in the reaction. Triglycerides which can be utilized in the hydrolysis reaction include triglycerides having $C_4$ to $C_{26}$ hydrocarbon chains with three fatty acid moieties. These materials can be derived from plants or animals or can be edible synthetic fats or oils. Liquid oils, e.g., unsaturated vegetable oils, can be used. Solid fats work only to the extent they are soluble in the solvent. These oils can be partially hydrogenated to convert some of the unsaturated double bonds of the fatty acid constituents into saturated bonds. Vegetable oils include soybean oil, hazelnut oil, linseed oil, olive oil, peanut oil, canola oil, safflower oil, rapeseed oil, cottonseed oil and sunflower seed oil can also be used herein.

Also suitable for use herein are the so-called low molecular weight synthetic fats which are certain tri- or diglycerides in which one or two of the hydroxyl groups of the glycerine have been esterified with acetic, propionic, butyric, hexanoic, capric or caprylic acids and one or two of the remaining hydroxyl groups of the glycerine have been esterified with a mixture of higher molecular weight fatty acids having from 8 to 22 carbon atoms. Especially preferred for use herein are symmetrical triglycerides as, e.g., tridecanoin or trioctanoin.

Other common types of triglycerides include: cocoa butter and cocoa butter substitutes, such as shea and illipe butter; milk fats, such as butter fat; and marine oils which can be converted into plastic or solid fats such as menhaden, pilcherd, sardine, whale and herring oils.

Preferred triglycerides are those derived from vegetable oils. These can be hydrogenated and unhydrogenated oils. Triglycerides of octanoic acid, decanoic acid and dodecanoic acid are preferred for use herein. Any unsaturated triglyceride containing unsaturated fatty acids is also preferred, e.g. triolein. The triglycerides of long chain fatty acids are usually not soluble in the hydrocarbon solvent or are solid at the reaction temperature. Therefore they are not preferred for use herein.

The aqueous solution of the enzyme is buffered to a pH of about 4 to about 8. Standard buffer solutions which are not incompatible with the enzyme can be used. These include the phosphate buffers.

The reaction mixture has the following proportions by weight percent:

| | |
|---|---|
| 3% to 40% | triglyceride |
| 15% to 25% | aqueous buffer |
| 10% to 25% | alcohol |
| 20% to 60% | hydrocarbon |

The preferred ratio of alcohol to triglyceride is based on the amount of fatty acid generated by the hydrolysis. The alcohol serves several functions in this reaction. It reacts with the fatty acid to make an alkyl ester driving the reaction toward the 2-acyl glyceride; and it modifies any association structures present in the reaction mixture. When the alcohol is insoluble in water, it can be substituted for the hydrocarbon if the triglyceride is soluble in the alcohol.

The reaction is carried out at ambient temperature or at temperatures of from about 20° C. to about 50° C. for from 0.5 hours to about 8 hours. The reaction is mixed using a standard laboratory mixer.

The hydrocarbon layer is separated from the aqueous phase. The 2-acylglyceride is present in the hydrocarbon phase. Any conventional separation technique can be used.

For example, the 2-acylglyceride can be isolated from the organic phase by crystallization or evaporation of the organic solvent. Liquid 2-acylmonoglycerides can be purified by distillation however, distillation frequently causes rearrangement or isomerization to 1-acyl-glycerides.

The 2-acylmonoglycerides can be esterified stereoselectively using acid anhydrides. It is not necessary to isolate the 2-monoacylglycerides from the organic phase if they are to be esterified. However, the solution should be dried to less than about 0.5% water to prevent hydrolysis of the acid anhydride. Any suitable drying agent such as magnesium sulfate, calcium chloride or other inert drying aid can be used. Excess anhydride could also be used, but this is less economical.

The excess lower alkyl alcohol should also be removed since it too can react with the acid anhydride to form the corresponding ester.

The 2-monoacylglyceride is reacted with an acid anhydride in an organic solvent. Any hydrocarbon, either alkyl or aromatic, or halogenated hydrocarbon can be used for this reaction. For example, petroleum ether, hexane, benzene, toluene, chloroform, methylene chloride and octane can be used.

A 1,3-specific lipase is added to the hydrocarbon mixture. The same lipases as were used to prepare the 2-acylmonoglycerides are suitable for this reaction.

They include immobilized lipases and liposomes which are preferred. Catalytic amounts of lipase are used.

Any acid anhydride can be used to esterify the 2-acylmonoglycerides. Acid anhydrides of alkyl fatty acids are commercially available or can be synthesized by conventional means.

The long chain fatty acids per se or naturally occurring fats and oils can serve as sources of the long chain saturated fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils.

The esterification is conducted at temperatures of from about 20° C. to reflux temperature of the solvent (about 50° C.). Usually the esterification takes about 1 hour to about 5 hours.

The mole ratio of acid anhydride to 2-acylmonoglyceride is from about 1:1 to about 3:1 anhydride to monoglyceride. Too large an excess of anhydride may cause formation of triglycerides instead of the stereospecific 1,2-diacyl glycerides or 2,3-diacyl glycerides.

If necessary, the 1,2-diacyl glyceride or 2,3-diglyceride can be isolated by precipitation or crystallization.

The regiospecific 1,2-diacyl glycerides or 2,3 diacyl glycerides can be converted to stereospecific triglycerides by any conventional esterification reaction. Such techniques include esterification with acid chlorides or acid anhydrides under essentially anhydrous conditions (0.5% or less water). Other catalytic reactions which are known not to cause rearrangement can be used. For example esterification with a fatty acid in the presence of 0.3% to about 1% (mole weight basis) of 4,-N,N-dimethyl-aminopyridine can be used to make stereospecific triglycerides from 1,2-diacylglycerides. Catalysts which are known to induce rearrangement should be avoided as they will cause the 1,2-diacyl glyceride, 2,3-diacyl glyceride or the resultant triglyceride to rearrange, thus producing a mixture of materials and not the regiospecific triglycerides that are desired.

The purified mixture of stereospecific triglycerides can also be subjected to bleaching and deodorizing steps for color and flavor/aroma improvement using conventional techniques well known in the fats and oils art. Alternatively, the reaction mixture can be bleached using conventional bleaching earth and/or activated carbon prior to purification. In the case of stereospecific triglycerides which have unsaturated fatty acid residues or mixtures of unsaturated and saturated fatty acid residues, the stereospecific triglycerides can be hydrogenated, before or after purification, to convert the unsaturated fatty acid residues to saturated fatty acid residues.

Uses of Stereospecific Triglycerides as Reduced Calorie Fats

Stereospecific triglycerides of the type MML/MLM obtained according to the present invention (where L is a long chain saturated fatty acid residue and M is a medium chain saturated fatty acid residue) can be used as reduced calorie fats to partially or totally replace normal triglyceride fat in any fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat.

EXAMPLE I

Preparation of 2-Decanoyl glycerol

Tridecanoin (45.0 mmole, 25.0 g) is dissolved in petroleum ether, b.p. 35° C.–60° C., (600 ml) and n-butanol (110 ml). This solution is mixed with 0.05 M phosphate buffer (110 ml) containing lipolase (Novo) 100L (9.0 g) and stirred at 37° C. for 3 hours. After separation of phases, the organic solution is evaporated at reduced pressure and temperature (below 30° C.) to a volume of about 100 ml. This solution is diluted with hexane (500 ml) and cooled to −78° C. using a dry ice-isopropanol bath. The precipitate is filtered below 0° C. and dried. Yield of 2-decanolyl glycerol is 7.2 g (65%).

EXAMPLE II

Preparation of 2-octanoyl glycerol is obtained from trioctanolyl glycerol (53.2 mmole 25.0 g) in the presence of lipase MAP from Amano (5.0 g) analogously to Example I with the yield 8.03 g (68%).

EXAMPLE III

Preparation of 1-Docosanolyl-1-decanolyl rac-glycerol

A mixture of 2-decanoyl glycerol from Example I (27.6 mmole, 6.8 g), docosanoic anhydride (30.2 mmole, 20.0 g) and immobilized IM-20 Lipozyme from Novo (11.4 g) in methylene chloride (500 ml) is refluxed for 2 hours. The lipozyme is from Novo. The enzyme is removed by filtration at room temperature. Upon cooling the filtrate to 0° C., docosanoic acid and anhydride precipitated and was filtered. The solution of product is further cooled to −78° C. using a dry ice/isopropanol bath. The product is filtered and dried. The yield of 1-docosanolyl-2-decanoyl rac-glycerol is 12.9 g (81.6%).

EXAMPLE IV

1-Docosanoyl-2-octanoyl rac glycerol is obtained from 2-octanoyl glycerol (27.5 mmole, 6.0 g) and docosanoic anhydride (28.5 mmole, 18.9 g) in the presence of immobilized IM-20 Lipozyme (10.0 g) analogously to Example III. However, instead of cooling the final solution of product, methylene chloride is evaporated and the residue is dissolved in hexane. On cooling to −78° C. the product precipitated. The yield after filtration was 9.67 g (65%).

EXAMPLE V

1-Docosanoyl-2-decanoyl-3-octanoyl rac-glycerol

A solution of 1-docosanoyl-2-decanoyl glycerol (24.6 mmole, 14.0 g), decanoic anhydride (26.8 mmole, 7.25 g) and 4-N,N-dimethylaminopyridine (DMAP) (1.25 mmole, 0.15 g) in methylene chloride (500 ml) is stirred at room temperature for 4 hours. Solvent is evaporated, the oily residue is dissolved in petroleum ether (500 ml) and cooled in dry ice. The precipitated product is filtered and dried under vacuum. Yield of 1-docosanoyl-2-decanoyl-3-octanoyl rac-glycerol is 13.8 g (81%).

EXAMPLE VI

1-Docosanoyl-2-octanoyl-3-decanoyl rac-glycerol is prepared from 1-docosanoyl-2-octanoyl rac-glycerol (18.5 mmole, 10.0 g) and decanoic anhydride (18.5 mmole, 6.05 g) with DMAP (0.5 g) analogously to Example V with the yield 11 g (85%).

EXAMPLE VII

2-Docosanoyl glycerol is obtained from 1,3-didecanoyl-2-docosanoyl glycerol (3.4 mmole, 2.5 g) in the presence of lipase MAP (2.0 g) analogously to Example 1. The time of hydrolysis in this case is 28 hours and the yield is 0.65 g (46%).

EXAMPLE VIII

1-Decanoyl-2-docosanoyl rac-glycerol is obtained from 2-docosanoyl glycerol (9.6 mmole, 4.0 g) and decanoic anhydride (9.6 mmole, 3.13 g) in the presence of immobilized Lipozyme (2.0 g) analogously to Example III with the yield 4.9 g (90%).

EXAMPLE IX

1-Decanoyl-2-docosanoyl-3-octanoyl rac-glycerol is prepared from 1-decanoyl-2-docosanoyl rac-glycerol (7.9 mmole, 4.5 g) and octanoic anhydride (7.9 mmole, 2.14 g) analogously to Example V with the yield 4.1 g (75).

What is claimed is:

1. A process for preparing 2-acylglycerides comprising:
   (A) mixing the following ingredients for at least one hour at a temperature of from 20° C. to 50° C.
      (1) from 15% to 25% of an aqueous buffer having a pH of from 4 to 8 containing a catalytic amount of 1,3-specific lipase enzyme;
      (2) from 20% to 60% of a water immiscible hydrocarbon;
      (3) from 3% to 40% of a triglyceride;
      (4) from 10% to 25% of a lower alkyl alcohol selected from the group consisting of methanol, 1-butanol, 2-butanol, 2-methyl-1-propanol, 3-methyl-1-propanol, and primary alkyl alcohols having 5 carbon atoms
      to form 2-acylglycerides;
   (B) separating the water immiscible hydrocarbon containing the 2-acylglyceride.

2. A process for preparing regiospecific 1,2-diacyl diglycerides or 2,3-diacyl diglycerides comprising the steps of:
   (1) preparing a 2-monoacylglycerides by a process comprising:
      (A) mixing the following ingredients for at least one hour at a temperature of from 20° C. to 50° C.:
         (i) from 15% to 25% of an aqueous buffer having a pH of from 4 to 8 containing a catalytic amount of 1,3-specific lipase enzyme;
         (ii) from 20% to 60% of a water immiscible hydrocarbon;
         (iii) from 3% to 40% of a triglyceride;
         (iv) from 10% to 25% of a lower alkyl alcohol selected from the group consisting of methanol, 1-butanol, 2-butanol, 2-methyl-1-propanol, 3-methyl-1-propanol, and primary alkyl alcohols having 5 carbon atoms
         to form 2-acylgyceride;
      (B) separating the immiscible hydrocarbon containing the 2-acylglyceride;
   (2) reacting said 2-acylmonoglyceride with an acid anhydride, a catalytic amount immobilized lipase in a water immiscible hydrocarbon for from 0.5 hours to 5 hours at a temperature of from 20° C. to 50° C. to form a stereoselective 1,2-diacyl diglyceride or 2,3-diacyl diglyceride.

3. A process according to claim 1 wherein said enzyme is immobilized on a support.

4. A process according to claim 3 wherein said hydrocarbon is selected from the group of consisting of alkyl hydrocarbons having from 5 to 10 carbons.

5. A process according to claim 4 wherein said triglyceride is selected from the group consisting of fatty acid triglycerides wherein said fatty acids have from 8 to 24 carbon atoms.

6. A process according to claim 5 wherein said triglyceride is selected from the group consisting of partially hydrogenated and unhydrogenated sunflower seed oil, soybean oil, canola, rapeseed oil, safflower oil, marine oils, corn oil and mixtures thereof.

7. A process according to claim 5 wherein said triglyceride contains octanoic acid or decanoic acid in the 2-position.

8. A process according to claim 2 wherein said alcohol is selected from the group consisting of methanol, 1-butanol, 1-pentanol and 2-methyl-1-propanol.

9. A process according to claim 8 wherein said enzyme is immobilized on a support.

10. A process according to claim 9 wherein said hydrocarbon is selected from the group of consisting of hexane, pentane, isooctane, petroleum ether and mixtures thereof.

11. A process according to claim 10 wherein said triglyceride is selected from the group consisting of fatty acid triglycerides wherein said fatty acids have from 8 to 24 carbon atoms.

12. A process according to claim 11 wherein said triglyceride is selected from the group consisting of partially hydrogenated and unhydrogenated sunflower seed oil, soybean oil, canola, rapeseed oil, safflower oil, marine oils, corn oil and mixtures thereof.

13. A process according to claim 12 wherein said triglyceride contains octanoic acid or decanoic acid in the 2-position.

14. A process according to claim 13 wherein said water-immiscible hydrocarbon in step 2 is selected from the group consisting of benzene, toluene, hexane, petroleum ether, methylene chloride, chloroform and mixtures thereof.

* * * * *